(12) United States Patent
Nessel (10) Patent No.: US 10,369,298 B2
(45) Date of Patent: Aug. 6, 2019

(54) SKIN-PATCH TYPE LARGE VOLUME BOLUS DRUG INJECTOR WITH MEDICAMENT PRE-HEATING

(71) Applicant: Sanofi, Paris (FR)

(72) Inventor: Christian Nessel, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 15/509,407

(22) PCT Filed: Sep. 11, 2015

(86) PCT No.: PCT/EP2015/070871
§ 371 (c)(1),
(2) Date: Mar. 7, 2017

(87) PCT Pub. No.: WO2016/041872
PCT Pub. Date: Mar. 24, 2016

(65) Prior Publication Data
US 2017/0259014 A1   Sep. 14, 2017

(30) Foreign Application Priority Data

Sep. 15, 2014  (EP) .................... 14306420

(51) Int. Cl.
*A61M 5/44*  (2006.01)
*A61M 5/168*  (2006.01)
(Continued)

(52) U.S. Cl.
CPC .......... *A61M 5/445* (2013.01); *A61M 5/1452* (2013.01); *A61M 5/14248* (2013.01);
(Continued)

(58) Field of Classification Search
CPC .......... A61M 5/14248; A61M 5/14244; A61M 5/445; A61M 2205/3368; A61M 2205/3613
See application file for complete search history.

(56) References Cited

U.S. PATENT DOCUMENTS 6,175,688 B1 * 1/2001 Cassidy ................ A61M 5/365
                                                    392/470
9,114,242 B2 * 8/2015 Fangrow ............ A61M 39/1011
(Continued)

FOREIGN PATENT DOCUMENTS

| WO | WO 2011/097487 | 8/2011 |
| WO | WO 2013/115843 | 8/2013 |
| WO | WO 2013/152323 | 10/2013 |

OTHER PUBLICATIONS

International Search Report and Written Opinion in International Application No. PCT/Ep2015/070871, dated Nov. 5, 2015, 15 pages.
(Continued)

*Primary Examiner* — Nathan R Price
*Assistant Examiner* — John A Doubrava
(74) *Attorney, Agent, or Firm* — Fish & Richardson P.C.

(57) ABSTRACT

A skin-patch type large volume drug delivery device (1) comprising a heat exchanger (24) to extract thermal energy from the body/skin surface of the user and to supply the extracted thermal energy to increase the temperature of the medicament. Alternatively or in addition, a Peltier element (35) can be used for the same purpose. The device includes a temperature sensor (31) and a controller (16) for varying the flow rate within the heat exchanger as a function of the drug temperature.

18 Claims, 5 Drawing Sheets

(51) Int. Cl.
*A61M 5/142* (2006.01)
*A61M 5/145* (2006.01)
*A61M 5/172* (2006.01)

(52) U.S. Cl.
CPC .... *A61M 5/16813* (2013.01); *A61M 5/16881* (2013.01); *A61M 5/172* (2013.01); *A61M 2005/14252* (2013.01); *A61M 2205/3368* (2013.01); *A61M 2205/364* (2013.01); *A61M 2205/3613* (2013.01); *A61M 2205/3673* (2013.01); *A61M 2205/50* (2013.01); *A61M 2205/8212* (2013.01)

(56) References Cited

U.S. PATENT DOCUMENTS

| | | | |
|---|---|---|---|
| 2003/0135250 A1* | 7/2003 | Lauman | A61M 5/44 607/104 |
| 2011/0270232 A1 | 11/2011 | Forsell | |
| 2012/0041391 A1* | 2/2012 | Fangrow | A61M 39/1011 604/246 |
| 2014/0276545 A1* | 9/2014 | Krogh Andersen | H05B 3/20 604/500 |
| 2015/0011965 A1* | 1/2015 | Cabiri | A61M 5/44 604/500 |
| 2016/0354555 A1* | 12/2016 | Gibson | A61M 5/40 |

OTHER PUBLICATIONS

International Preliminary Report on Patentability in International Application No. PCT/EP2015/070871, dated Mar. 21, 2017, 9 pages.

\* cited by examiner

SKIN-PATCH TYPE LARGE VOLUME BOLUS DRUG INJECTOR WITH MEDICAMENT PRE-HEATING

CROSS-REFERENCE TO RELATED APPLICATIONS

This application is a U.S. national stage application under 35 USC § 371 of International Application No. PCT/EP2015/070871, filed on Sep. 11, 2015, which claims priority to European Patent Application No. 14306420.2 filed on Sep. 15, 2014, the entire contents of which are incorporated herein by reference.

FIELD

This specification relates to a device for increasing the temperature of medicament before it is delivered to a patient. Particularly, but not exclusively, the specification relates to a device in which a heat exchanger extracts thermal energy from the body of the patient and transfers the thermal energy into a medicament to warm the medicament before it is delivered to the patient.

BACKGROUND

Injection or infusion pumps of the type known as patch pumps for delivering injections of medicament are known in the art. Another type of injection pump that is gaining traction is the bolus injector device.

Some bolus injector devices are intended to be used with relatively large volumes of medicament, typically at least 1 ml and maybe a few ml. Injection of such large volumes of medicament can take some minutes or even hours. Such high capacity bolus injector devices can be called large volume devices (LVDs).

To use a patch pump or bolus injector device such as an LVD, it is first supported on a suitable injection site of a patient and, once installed, injection is initiated by the patient or another person. The device is generally worn against the skin and held in place using a suitable fastener.

Devices of this type, as well as the medicament that they deliver, are commonly stored at relatively low ambient temperatures immediately before use. The medicament may, for example, be stored in a refrigerator at about 4° C. Injecting a liquid medicament at about 4° C. into the body can cause discomfort for the patient.

SUMMARY

According to aspects of the disclosure, there is provided a device configured to deliver a medicament to a user by injection, comprising a heat exchanger configured to extract thermal energy from the body tissue of the user through the skin of the user and to supply the extracted thermal energy to increase a temperature of the medicament.

The extraction of thermal energy from the body tissue of the user allows the extracted thermal energy to be used to heat the medicament in the device. This may mean that the device's weight and/or size can be reduced by the absence, or reduction in size, of a battery or other power source in the device. The cost of producing the device may also be reduced.

The heat exchanger may comprise a medicament flow path formed of thermally conductive material in a patient contact region of the device that in use is supported against skin of the user.

The thermally conductive material may increase the efficiency of the transfer of thermal energy into the medicament.

The medicament flow path may comprise a winding path in the patient contact region of the device.

The winding path may increase the effective surface area of the heat exchanger and, thereby, allow an increase in the rate at which body heat can be transferred into the medicament. The time taken to warm-up the medicament may be reduced.

The medicament flow path may comprise a liquid impermeable membrane to allow gas but not liquid medicament to be expelled through the membrane.

The membrane may mean that the heat exchanger cannot fill with air. Priming of the heat exchanger, for example by pumping out air before operation, is made redundant.

The heat exchanger may comprise a Peltier element.

The Peltier element may increase the rate of at which thermal energy can be extracted from the body tissue. This may increase the rate at which the medicament can be heated. The time taken to warm-up the medicament may be reduced.

The medicament may be thermally coupled to the Peltier element to act as a heat sink for thermal energy extracted from the body tissue of the user by the Peltier element.

The thermal coupling increases the efficiency with which thermal energy transfers from the Peltier element to the medicament. This avoids loss of thermal energy and may increase the efficiency of the Peltier element.

The device may comprise a medicament temperature sensor configured to sense a temperature of the medicament in the device.

The temperature sensor may enable the device to actively determine when is most appropriate to release the heated medicament for injection. For example, the sensor may enable the device to accurately heat the medicament to body temperature before injection. The sensor may increase the reliability of the device in terms of producing a consistent medicament temperature for the patient.

The device may be configured to commence delivery of the medicament in response to the temperature sensor sensing that the medicament has reached a predetermined temperature.

This may enable the device to consistently deliver medicament at a temperature which is predictable and/or expected by the patient.

The device may comprise a flow control apparatus configured to control a rate of delivery of the medicament in response to the temperature of the medicament sensed by the temperature sensor.

This may enable the device to keep the temperature of injected medicament reasonably constant, for example based on a temperature differential across the heat exchanger. This may lead to a more consistent experience for patient.

The flow control apparatus may be configured to increase the rate of delivery in a manner which is proportional to increases in the sensed temperature of the medicament.

This control of the rate of delivery may ensure no overheating of the medicament takes place in the device.

The flow control apparatus may be configured to decrease the rate of delivery in a manner which is proportional to decreases in the sensed temperature of the medicament.

This control of the rate of delivery may ensure that no under-heating takes place in the device.

The flow control apparatus may comprise a flow restrictor element located in the heat exchanger configured to vary the size of a flow path through the device to vary the rate of delivery of the medicament.

The flow restrictor element may enable the device to vary the medicament flow rate, for example to provide a consistent patient experience in terms of the temperature of injected medicament.

The flow control apparatus may comprise a medicament pump configured to pump medicament through the heat exchanger.

The pump may enable the device to vary the medicament flow rate, for example to provide a consistent patient experience in terms of the temperature of injected medicament.

The device may be wearable.

This allows the device to be fastened to the patient during an injection and may improve the consistency and/or efficiency of thermal energy transfer from the body of the patient to the medicament.

The device may comprise a timing element to trigger release of heated medicament for injection into the user.

This may allow the heat exchanger to operate without being controlled by a controller, such as a microcontroller. This may reduce the cost of producing the device.

The device may be a Bolus Injector device.

According to aspects of the disclosure, there is provided a system comprising the device and a reservoir of medicament to be delivered into the user by injection.

According to aspects of the disclosure, there is provided a method of increasing a temperature of a medicament in a device configured to deliver the medicament to a user by injection, comprising extracting thermal energy from the body tissue of the user using a heat exchanger and supplying the extracted thermal energy to increase the temperature of the medicament.

BRIEF DESCRIPTION OF THE FIGURES

For the purpose of example only, embodiments are described below with reference to the accompanying figures in which.

DETAILED DESCRIPTION

A wearable fluid delivery device for delivering fluid medicament to a patient is described below. The device comprises a reservoir for storing a quantity of medicament and a dispensing interface for delivering the medicament to the patient. The device is configured to deliver the medicament from the dispensing interface by injection and to warm the medicament before commencing the injection using thermal energy extracted from the body of the patient. The warming of the medicament and the injection take place whilst the device is being worn against the patient's skin.

Figure 1:
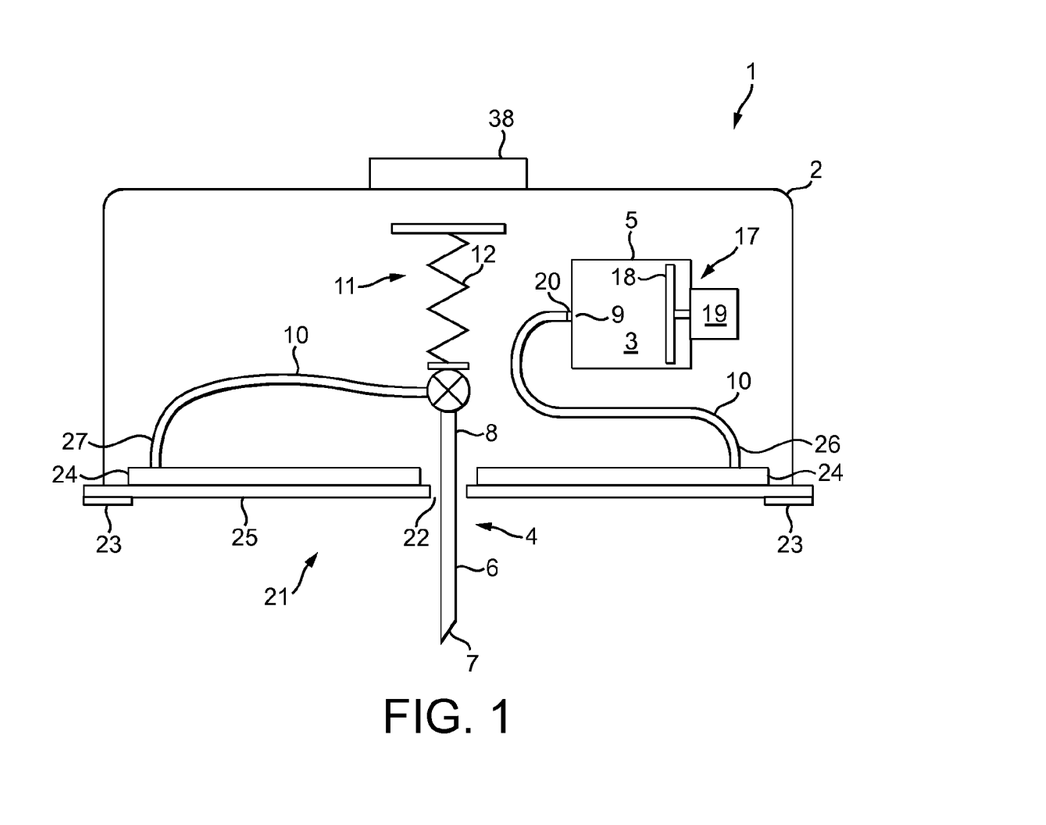
FIG. 1 is a schematic illustration of a wearable device for delivering medicament to a user by injection, in which a heat exchanger heats the medicament using thermal energy extracted from the body of the user, according to an exemplary embodiment.

The device is described below in the context of a bolus injector, but it will be appreciated that it could alternatively be another type of Large Volume Device (LVD). Referring to FIG. 1, the device 1 comprises a protective housing 2 in which the reservoir of medicament 3 and the dispensing interface 4 are located together with other components of the device 1. The housing 2 is formed from moulded plastics or another suitable material. The reservoir of medicament 3 is provided in a capsule 5, which may contain a single dose of the medicament. The capsule 5 is formed of inert material such as glass and is secured inside an internal cavity of the housing 2. The capsule 5 may be replaceable to allow re-use of the device 1. Alternatively, the capsule 5 may be non-replaceable in the device 1 so that, once the contents of the capsule 5 has been exhausted, the device 1 can no longer be used to deliver medicament and must be disposed of. This single-use nature of the device 1 facilitates ease of operation and improves safety by ensuring that a patient cannot mistakenly install an incorrect replacement capsule.

The dispensing interface 4 comprises an injection element for injection of the medicament from the device 1 into the patient. The injection element is explained below in the context of a cannula 6, as illustrated in FIG. 1, although it will be appreciated that other types of injection element could alternatively be used. Examples of alternative injection elements are discussed further below.

The cannula 6 comprises a distal end 7, which during use protrudes through the housing 2 of the device 1 into the body tissue of the patient. The cannula 6 also comprises a proximal end 8, which is arranged to receive medicament from the reservoir 3 referred to above. For example, an opening 9 in the form of an exit port in the capsule 5 may allow medicament to flow out of the capsule 5 and, ultimately, into the proximal end 8 of the cannula 6. The opening 9 in the capsule 5 is connected to the proximal end 8 of the cannula 6 by a flow channel, which is at least in part provided by a conduit 10 connected to the opening 9 and the proximal end 8 of the cannula 6. This is described in more detail below.

The cannula 6 may be controllably extendable and/or retractable through the exterior of the housing 2 in order to allow it to be safely stowed in the housing 2 when not in use. The device 1 may contain a user-operable actuator 11 to facilitate this. The actuator 11 is configured to cause movement of the cannula 6 relative to the housing 2 of the device 1 in order to extend and/or retract the cannula 6. An example is an actuator 11 that comprises a sprung element 12 and a switch 13 for releasing the sprung element 12. Upon release by the switch 13, the sprung element 12 may be configured to automatically extend and thereby drive the cannula 6 partially out of the housing 2 into an injection position. The actuator 11 may be electrically powered. For example, the switch 13 for releasing the sprung element 12 referred to above may be electrically powered. Electrical power may also be used to retract the sprung element 12 back to its original non-extended position, thereby also withdrawing the cannula 6. For this purpose, the actuator 11 may comprise an electrical motor 14 and a suitable drive mechanism coupled to the sprung element 12. The electrical power may be provided by a battery 15 or other power source in the device 1, which may be rechargeable.

In particular, the battery 15 may be rechargeable if the configuration of the device 1 is such that the capsule 5 of medicament is replaceable. In this type of configuration, the device 1 comprises a sterile part and a non-sterile part. The sterile part of the device 1 is replaceable and comprises the replaceable capsule 5. The non-sterile part of the device 1 is reusable and comprises reusable elements of the device 1. The elements in the non-sterile part may include, for example, a rechargeable battery 15. In general, the non-sterile part includes elements that do not need to be sterile for safe operation of the device 1 and can be safely reused. It will be appreciated, however, that there is no requirement for the elements that do not need to be sterile to be confined exclusively to the non-sterile part of the device 1. For example, it is possible for the battery 15 to be included with other replaceable elements in the sterile part of the device 1. In this configuration, the battery 15 is non-rechargeable since it is replaced each time the capsule 5 is replaced.

As will be explained in more detail below, the device 1 may comprise an electronic controller 16 which is configured to control operation of the actuator 11 and/or other elements of the device 1. The electronic controller 16 comprises a processor and a memory and may, for example, comprise an electronic microcontroller which is communicatively coupled to the actuator 11 and/or other elements of the device 1 using a system bus (not shown). The switch 13, motor 14, battery 15 and controller 16 are shown in the block diagram of the device 1 in FIG. 2, but are not shown in FIG. 1.

An alternative is for the actuator 11 to operate under the control of a timing element, such as a mechanical timer. The timing element may be a count-down timer. The elapse of a count-down period of the timing element may indicate that an event has occurred, such as the completion of an injection of a dose of medicament. The elapse of the count-down period may cause the actuator 11 to move the cannula 6 or other injection element, for example by withdrawing the cannula 6 back into the housing 2 of the device 1.

The distal end 7 of the cannula 6 may be sharpened to facilitate its insertion into the body tissue of the patient. Alternatively, the dispensing interface 4 may also comprise a separate needle (not shown) for aiding the insertion of the distal end 7 of the cannula 6 into the body tissue. In this case, the cannula and the needle may together form a trocar. The needle may be controllably extendable and/or retractable from the housing 2 of the device 1 in a similar manner to the cannula 6 discussed above. The needle is configured to break the skin of the patient in order to allow the cannula 6 to move into the body tissue. The needle may, for example, be arranged to extend through the centre of the cannula 6. Once the skin has been broken, the device 1 is configured to retract the needle back into the housing 2 before delivery of the medicament. In the case that the device 1 comprises a separate needle of the type described above, the device 1 may comprise an actuator similar to the one previously discussed in relation to the cannula 6 to facilitate the extension and retraction of the needle.

Another alternative is for the medicament to be delivered through the needle itself. In this case, the needle has properties which are similar to those of conventional injection needles. A proximal end of the needle is connected to the medicament reservoir 3 in a similar manner to the cannula 6 discussed above so that fluid medicament can flow through the needle into the body tissue of the patient. If the device 1 is configured in this manner, the cannula 6 may be omitted from the dispensing interface 4.

The flow of medicament into the cannula 6, or other injection element, is controlled by a flow control apparatus 17. As illustrated in FIG. 1, the flow control apparatus 17 may comprise a piston 18 which is moveable through the capsule 5 from one end to the other to drive medicament out of the capsule 5 through the opening 9 referred to above. A suitable drive mechanism (not shown) is mechanically coupled to the piston 18 and is operable to cause the piston 18 to move through the capsule 5. Movement of the piston 18 may be electrically powered. For example, an electric motor 19 may be connected to the drive mechanism. The electric motor 19 is powered by a power source in the device 1, such as the battery 15 referred to previously.

Additionally or alternatively, the flow control apparatus 17 may comprise a seal 20 at the opening 9 in the capsule 5 to prevent medicament from flowing out of the capsule 5 before it is intended that it should do so. The seal 20 is breakable, or openable in some other way, to allow medicament to move from the capsule 5 into the cannula 6 or other injection element via the conduit 10 referred to previously. The device 1 is configured to operate the flow control apparatus 17, for example by breaking the seal 20 and/or moving the piston 18, in response to a patient-initiated trigger, as explained below.

Figure 3:
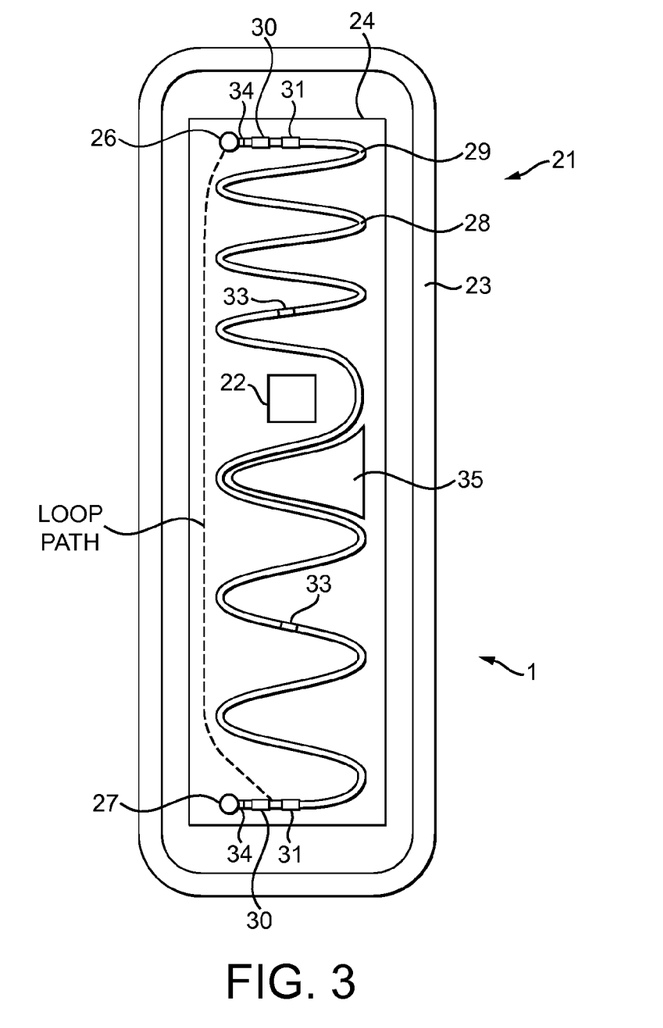
FIG. 3 is a schematic illustration of a patient contact region of a wearable device for delivering medicament to a user by injection, in which a heat exchanger heats the medicament using thermal energy extracted from the body of the user, according to an exemplary embodiment.

Referring to FIG. 3, a contact region 21 of the housing 2 is arranged to be worn against the skin of the patient during use of the device 1. The contact region 21 may, for example, be located on a bottom face of the housing 2. The contact region 21 has geometric and tactile properties that are selected to be comfortable when worn against the skin of the patient. It is through the contact region 21 of the housing 2 that the cannula 6, or other injection element, protrudes into the body tissue of the patient during delivery of the medicament. The contact region 21 may, for example, comprise an aperture 22 through which the cannula 6 protrudes during use of the device 1. The aperture 22 is large enough to accommodate the cannula 6 and/or the separate needle referred to above, including during the extension and retraction operations previously described.

During use of the device 1, the contact region 21 is held against the skin of the patient by a fastener. The fastener is suitable for holding the contact region 21 in a stable position against the skin for a significant period of time, such as several hours, in order to ensure that the injection element is at all times maintained in a fixed position relative to the body of the patient during use of the device 1. As shown in FIGS. 1 and 3, an example of a suitable fastener is an adhesive layer 23 for temporarily adhering the contact region 21 to the skin of the patient. The adhesive layer 23 may comprise a standard biocompatible glue, as used in common adhesive bandages. In order to protect the adhesive layer 23 from damage and to prevent it from sticking to unwanted objects prior to it being attached to the skin of the patient, the contact region 21 of the device 1 also includes a protective covering (not shown) which overlies the adhesive layer 23. The protective covering is selectively removable from the contact region 21 in order to expose the adhesive layer 23 before use of the device 1, for example by peeling the covering away from the adhesive layer 23.

The device 1 also comprises a heat exchanger 24 for heating the medicament in the device 1 before the medicament is delivered into the body tissue of the patient. The heat exchanger 24 is configured to take advantage of temperature differentials between the body of the patient and the medicament in the capsule 5 to increase the temperature of the medicament in the device 1 before it is injected into the patient. In particular, the heat exchanger 24 is configured to extract thermal energy from the body of the patient and to use the extracted thermal energy to increase the temperature of the medicament.

For example, the heat exchanger 24 may be configured to warm the medicament to body temperature before the medicament is injected into the patient via the cannula 6. This provides a more comfortable injection experience for the patient. The thermal energy used to heat the medicament in the heat exchanger 24 may be extracted entirely from the body of the patient. Extracting thermal energy from the body of the patient rather than generating the thermal energy by other means reduces power consumption in the device 1 and also reduces the necessary storage capacity of the battery 15 or other power source. This in turn means that the device 1 can be smaller and lighter than if alternative solutions were used to heat the medicament, such as an electrically resistive heating element.

The contact region 21 and the delivery interface 4 described previously may be shaped and sized to facilitate high efficiency transfer of thermal energy between the heat exchanger 24 and the body of the patient, for example by high efficiency thermal contact.

As shown in FIGS. 1 and 3, the heat exchanger 24 is located in the contact region 21 of the device 1 in a position which is adjacent to the skin tissue of the patient. The heat exchanger 24 comprises a thermally conductive patient interface surface 25. The location and alignment of the patient interface surface 25 is such that it is in direct contact with the skin tissue of the patient when the device 1 is fastened to the patient in the manner previously described. The surface area of the patient interface surface 25 may be large and may comprise at least fifty percent of the total surface area of the contact region 21. This facilitates a large volume of thermal energy transfer through the surface 25. An example of the surface is illustrated in FIG. 1.

Figure 4:
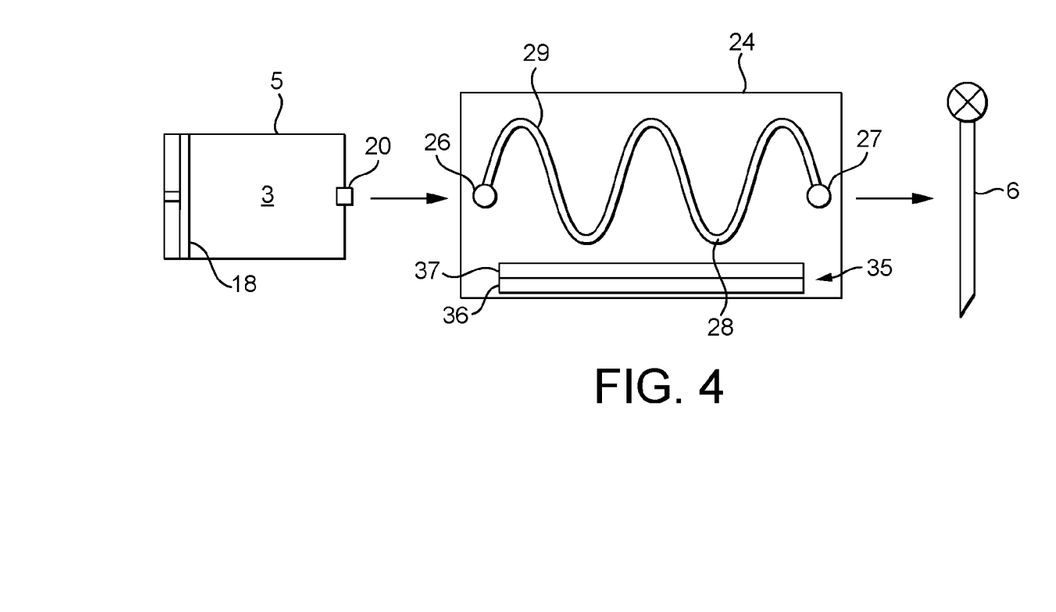
FIG. 4 is a schematic diagram showing a flow path of medicament through a heat exchanger in a wearable device for delivering medicament to a user by injection, according to an exemplary embodiment.

A schematic diagram of a flow of medicament through device 1, including through the heat exchanger 24, is illustrated in FIG. 4. As can be seen from FIG. 4, the medicament may flow into an entry port 26 of the heat exchanger 24 from the capsule 5. For example, the flow control apparatus 17 referred to above may be configured to dispense a single of dose of medicament from the capsule 5 into the heat exchanger 24 by movement of the piston 18. The dose of medicament is warmed in the heat exchanger 24 by thermal energy that has been extracted from the body of the patient, before being allowed to flow out of an exit port 27 of the heat exchanger 24 into the cannula 6. The connection between the capsule 5 and the entry port 26 of the heat exchanger 24 is provided by a first length of the conduit 10 referred to previously. Similarly, the connection between the exit port 27 of the heat exchanger 24 and the proximal end 8 of the cannula 6 is provided by a second length of the conduit 10.

As illustrated schematically in FIGS. 3 and 4, the heat exchanger 24 comprises a medicament flow channel 28 along which medicament received through the entry port 26 flows through the heat exchanger 24. The medicament flow channel 28 may for example be provided by a pipe 29 which guides the medicament along a path through the heat exchanger 24. The path is an indirect path, in the sense that it does not pass along the shortest route between the entry port 26 and the exit port 27. The path instead takes a winding route through the heat exchanger 24 so that the length of the channel 28 and, therefore, the time spent by the medicament in the channel 28, is longer than would be the case if the path extended directly between the entry and exit ports 26, 27.

The bottom surface of the pipe 29 may form all or part of the patient interface surface 25, so that it is in direct contact with the skin of the patient when the device 1 is fastened in place for use. Alternatively, the pipe 29 may be located directly behind, and in contact with, the patient interface surface 25.

It will be appreciated that the body temperature of the patient is likely to be higher than the ambient temperature at which the device 1, and particularly the medicament in the capsule 5, has been stored. The result of this is that the temperature of the medicament in the device 1 is likely to be initially lower than the body temperature of the patient. This causes thermal energy to naturally flow through the thermally conductive walls of the pipe 29 from the body of the patient into the medicament inside the pipe 29, thereby increasing the temperature of the medicament. This process will continue until the temperature of the pipe 29 is equal to the temperature of the region of skin tissue against which the heat exchanger 24 is located.

The pipe 29 is formed of highly thermally conductive material to facilitate efficient transfer of thermal energy through the walls of the pipe 29. This increases the rate at which thermal energy can flow from the skin tissue of the patient into the medicament inside the pipe 29 and therefore the rate at which the medicament is warmed in the heat exchanger 24. The profile of the pipe 29 may be substantially flat so as to maximise the surface area of the pipe 29 which is in direct contact with, or in close proximity to, the skin tissue of the patient. The surface of the pipe 29 may include protrusions or indentations, for example in the form of dimples, to increase the surface area of the pipe 29 and thereby promote the transfer of thermal energy through the pipe 29 into the medicament.

Referring to FIG. 3, the heat exchanger 24 may comprise a valve 30 at each of the entry and exit ports 26, 27. These valves 26, 27 can be selectively opened and closed, for example under the control of the controller 16, to control the flow of medicament into or out of the heat exchanger 24. Specifically, if the valve 30 at the entry port 26 is closed, no medicament can flow into or out of the heat exchanger 24 through the exit port 26. The same applies for the valve 30 at the entry port 27. The medicament flow channel 28 in the heat exchanger 24 may, for example, comprise a loop around which the medicament circulates when both valves 30 are closed. This loop is illustrated by the dashed line in FIG. 3.

The heat exchanger 24 may also comprise one or more temperature sensors 31 configured to sense the temperature of the medicament in the flow channel 28 of the heat exchanger 24. The temperature sensors 31 are illustrated schematically in FIG. 3 and may, for example, comprise one or more thermocouples or other suitable sensors located in the flow channel 28. The sensor(s) 31 are configured to communicate the sensed temperature of the medicament to the controller 16 via a communication coupling between the heat exchanger 24 and the controller 16. This allows the controller 16 to monitor the temperature of the medicament in the heat exchanger 24 and to control the operation of the valves 30 accordingly. In particular, the controller 16 may be configured to close the valves 30 upon a dose of medicament being dispensed from the capsule 5 into the heat exchanger 24 and to retain the medicament in the heat exchanger 24 until the temperature sensor(s) 31 indicate that the medicament has been heated to a predetermined temperature. This predetermined temperature may be pre-stored in the memory of the controller 16, or may be set by the patient or a medical professional using suitable controls on the device 1. An example of such a temperature is body temperature, i.e. approximately 37° C.

Upon receiving an indication that the sensed temperature of the medicament in the heat exchanger 24 has reached the predetermined temperature, the controller 16 may be configured to cause the valve 30 at the exit port 27 to open so that the heated medicament can flow through the second length of conduit 10 into the proximal end 8 of the cannula 6. The valve 30 at the entry port 26 may be kept closed to prevent any of the heated medicament from flowing back towards the capsule 5.

Figure 2:
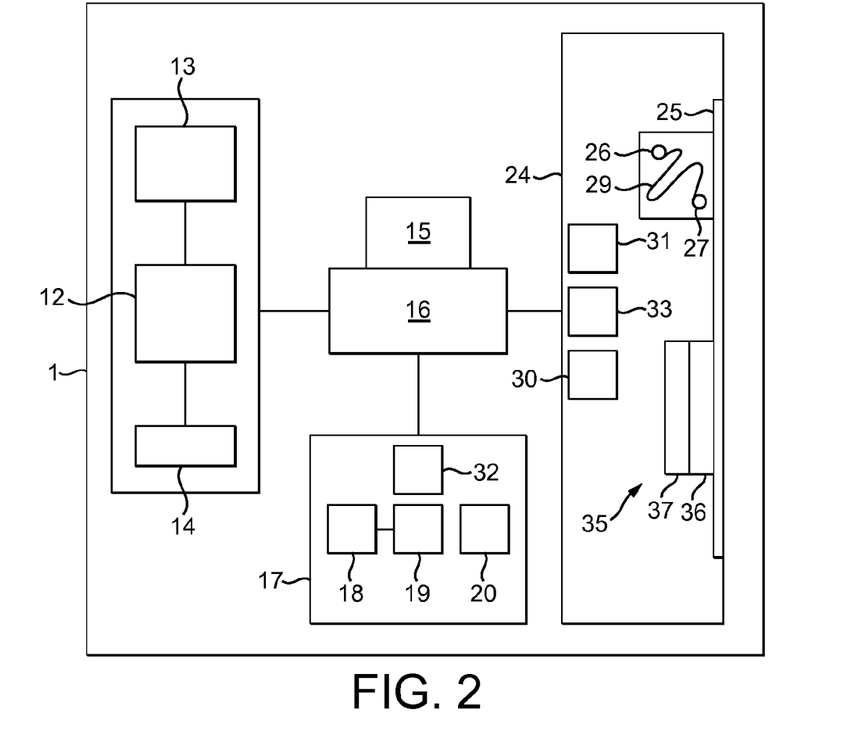
FIG. 2 is a block diagram of a wearable device for delivering medicament to a user by injection, in which a heat exchanger heats the medicament using thermal energy extracted from the body of the user, according to an exemplary embodiment.

The flow of medicament through the heat exchanger 24 and/or from the heat exchanger 24 to the proximal end 8 of the cannula 6 via the second length of conduit 10 may be caused by a pump 32 of the flow control apparatus 17. The pump 32 is schematically illustrated in FIG. 2 and may, for example, comprise an electrical pump 32 located in the heat exchanger 24. The pump 32 is configured to pump liquid medicament out of the heat exchanger 24 through the exit port 27 and into the cannula 6. The pump 32 operates under the control of the controller 16. The rate at which the medicament is pumped into the cannula 6 can be prestored in the controller 16 so that the medicament is delivered in a specified manner, over a specified time period.

The controller 16 may be configured to vary the rate at which the medicament is pumped, or otherwise released, into the proximal end 8 of the cannula 6 in dependence of a temperature of the medicament sensed by a temperature sensor 31 at the exit port 27. For example, if the valves 30 referred to above are not included in the device 1, or are both open, the medicament is retained in the heat exchanger 24 only for the amount of time that it takes to flow through the flow channel 28 between the entry port 26 and the exit port 27. The amount of thermal energy transferred into the medicament, and thus the temperature of the medicament, at the exit port 27 is dependent on the time that the medicament has spent in the heat exchanger 24 and so, if signals from the temperature sensor 31 at the exit port 27 indicate that the temperature of the medicament is below a threshold level, the controller 16 may be configured to reduce the flow rate of the medicament through the flow channel 28. This increases the time spent by the medicament in the heat exchanger 24 and, thereby, increases the amount of thermal energy transferred into the medicament before it reaches the exit port 27.

Likewise, if signals from the temperature sensor 31 at the exit port 27 indicate that the temperature of the medicament is above a threshold level, the controller 16 may be configured to increase the flow rate of the medicament through the flow channel 28 to reduce the amount of thermal energy received by the medicament in the heat exchanger 24.

The flow rate of the medicament in the heat exchanger 24 may additionally or alternatively be controlled in dependence of a temperature differential between the temperature of the medicament sensed by a temperature sensor 31 at the entry port 26 and the temperature of the medicament sensed by a temperature sensor 31 at the exit port 27. The controller 16 may, for example, vary the flow rate of the medicament in the heat exchanger 24 with the aim of obtaining a preset temperature difference between the entry and exit ports 26, 27. An example of such a temperature difference is an increase of between 5° C. and 10° C. between the entry port 26 and exit port 27.

The controller 16 may vary the flow rate of the medicament in the heat exchanger 24 by partially closing or opening the valve 30 at the exit port 27. Additionally or alternatively, the controller 16 may operate a flow restricting element 33 of the flow control apparatus 17 to reduce the size of the flow channel 28 at one or points in the pipe 29. Additionally or alternatively, the flow rate of medicament may be varied by appropriate operation of the pump 32.

The heat exchanger 24 may comprise an air impermeable membrane 34 at the entry and exit ports 26, 27 to prevent air from entering the flow channel 28 and subsequently being pumped through the cannula 6 with the medicament. Alternatively, the device 1 may be configured to prime the heat exchanger 24 before medicament is released into it from the capsule 5 by causing air in the flow channel 28 to be expelled. This may comprise pumping air out of the exit port 27 using the pump 32 referred to previously.

In addition or as an alternative to the pipe 29 referred to above, the heat exchanger 24 may comprise one or more thermoelectric heating elements configured to heat the medicament. The thermoelectric heating elements may be provided as part of a thermoelectric heating device.

The thermoelectric device is described below in the context of a Peltier device 35, but it will be appreciated that other types of thermoelectric devices may be used. The Peltier device 35 comprises one or more Peltier elements and is arranged to extract thermal energy from the body of the patient. The heat exchanger 24 is configured to use the extracted thermal energy to increase the temperature of the medicament in the heat exchanger 24.

The Peltier device 35 is thermally coupled to the skin of the patient and is configured to transfer thermal energy out of the skin tissue of the patient. This may occur either through thermally conductive contact with the patient's skin tissue, for example via the patient interface surface 25, or through thermal convection or conduction through a suitable intermediate heat transfer medium such as a thermally conductive gel. The device 35 comprises a patient interface material 36 which is an electrically and thermally conductive material. The patient interface material 36 is electrically connected to a different electrically and thermally conductive material 37 on the opposite side of the device 35. The Peltier device 35 is configured to cause an electrical current to flow across the junction between the materials 36, 37 to generate a difference in temperature between the materials 36, 37 due to the Peltier effect. Using this effect, the Peltier device 35 is configured to control the temperature of the patient interface material 36 to a high degree of accuracy by monitoring the temperature of the interface material 36 and applying an appropriate electrical voltage across the junction between the materials 36, 37.

The temperature of the patient interface material 36 is detected by a temperature sensor, for example in the form of a thermistor, which is located in close proximity to the surface of the material 36. Using signals from this temperature sensor, the Peltier device 35 adjusts the voltage applied across the junction between the different materials 36, 37, and thereby the temperature of the patient interface material 36, to obtain a desired value at the temperature sensor. The Peltier device 35 may do this under the control of the controller 16. For example, the desired temperature of the patient interface material 36 at any given time may be communicated to the Peltier device 35 by the controller 16 based on prestored values and the information being fed to the controller 16 by the temperature sensors 31 in the heat exchanger 24. In this way, the controller 16 is configured to cause the Peltier device 35 to extract an appropriate amount of thermal energy from the body of the patient to heat the medicament.

The Peltier device 35 is configured to use the medicament as a heat sink into which thermal energy extracted from the patient interface material 36 is transferred. The Peltier device 35 may, for example, be located adjacent to the flow channel 28 so as to transfer thermal energy directly into the wall of the pipe 29 referred to previously. A suitable thermal contact between the Peltier device 35 and the pipe 29 is arranged to facilitate this transfer of thermal energy in an efficient manner.

Alternatively, the Peltier device 35 may be arranged to transfer thermal energy extracted from the body of the patient directly into the medicament in the capsule 5. In this way, the medicament can be heated before it is dispensed from the capsule 5 by the flow control apparatus 17. A thermally conductive element (not shown) connected between the Peltier device 35 and a thermally conductive region of the capsule 5 may be provided to facilitate the transfer of energy. In this embodiment, suitable temperature sensors, similar to those discussed above in relation to the entry and exit ports 26, 27, may be provided in the capsule 5 so that the temperature of the medicament in the capsule 5 can be fed back the controller 16 via a communication coupling. This allows the option for the controller 16 to open the seal 20 in the capsule 5 only when the temperature of the medicament in the capsule 5 has reached a predetermined temperature, such as within 5° C. of the body temperature of the patient.

Figure 5:
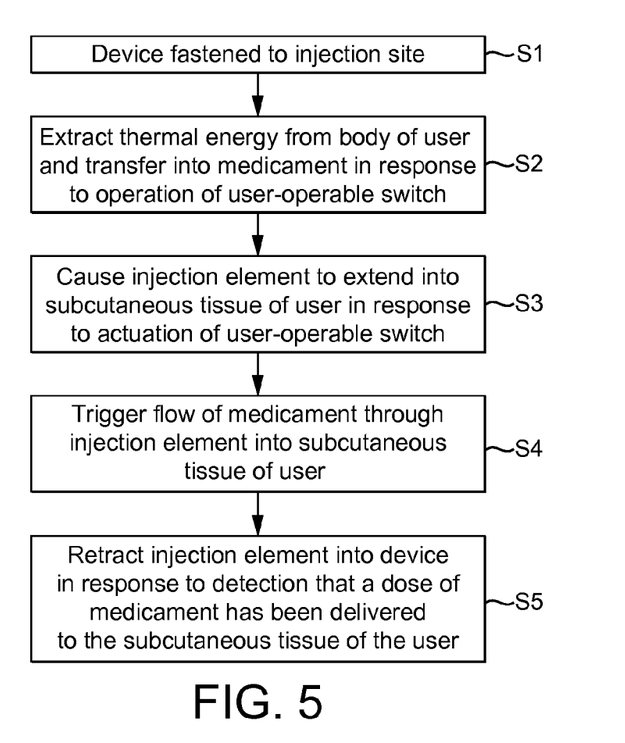
FIG. 5 is a flow diagram of a method of heating a medicament before it is delivered into the body of a patient, according to an exemplary embodiment.

An example of a medicament heating and injection process is described below with respect to FIG. 5. In a first step S1, the patient fastens the contact region 21 of the device 1 to an injection site on his or her body. The patient may, for example, peel the protective covering away from the adhesive layer 23 and press the adhesive layer 23 against his or her skin to adhere the device 1 to the injection site.

In a second step S2, the patient actuates a switch 38 on the housing 2 of the device 1 to begin delivery of the medicament. In response to the switch being actuated, the flow control apparatus 17 is configured to dispense a dose of medicament into the flow channel 28 of the heat exchanger 24 via the first length of conduit 10. For example, the controller 16 may cause power to be supplied from the battery 15 to the electric motor 19 coupled to the piston 18 in the capsule 5. The electric motor 19 drives movement of the piston 18 through the capsule 5 to expel a dose of medicament through the opening 9 in the far end of the capsule 5. If the flow control apparatus 17 comprises a seal 20 at the opening 9 of the capsule 5, this seal 20 is opened to allow the fluid medicament to be released into the first length of conduit 10. The seal 20 may be broken by fluid pressure in the capsule 5 caused by movement of the piston 18 or may be broken by some other means, such as an actuator (not shown) which moves in response to a signal from the controller 16 to pierce the seal 20.

The medicament is heated by the heat exchanger 24 in the manner described above, for example until it reaches a threshold temperature. An example of a threshold temperature is within approximately 5° C. of the body temperature of the patient.

In a third step S3, the device 1 is configured to cause the cannula 6 or other injection element to extend through the aperture 22 in the housing 2 and into the body tissue of the patient. This may take place a predetermined period of time following the actuation of the switch 38 or in response to it being detected that the medicament has been heated to a predetermined temperature. The device 1 may optionally comprise a sensor (not shown) that is configured to detect the position of the cannula 6 or other injection element and report to the controller 16. In this way, the controller 16 is informed of when the cannula 6 or other injection element has been fully extended through the aperture 22 in the housing 2 and is in position to inject the medicament into the body tissue.

In a fourth step S4, the controller 16 triggers a flow of medicament into the proximal end 8 of the cannula 6. This may involve the medicament flowing into the cannula 6 from the heat exchanger 24, as previously described. The fourth step S4 may be triggered in response to it being detected that the medicament has reaches a predetermined temperature or has been in the heat exchanger 24 for a predetermined amount of time. Alternatively, the fourth step S4 may be triggered in response to it being detected that the cannula 6 has been extended into the patient. The dose may be administered to the patient in a continuous way at a pre-set rate. Alternatively, the dose may be administered to the patient in a plurality of discrete portions over a pre-set time period, or in any other manner, for example by appropriate movements of the piston 18 or operation of the pump 32. The device 1 may be configured to deliver the dose of medicament in a manner and at a rate which is dictated by the controller 16.

In a fifth step S5, the controller 16 is configured to cause the actuator 11 to retract the cannula 6 out of the body tissue of the patient to end the medicament delivery process.

It will be appreciated that the alternatives described can be used either singly or in combination.

Although the device 1 has been described in terms of comprising an automatically extending/retracting injection element, it will be appreciated that the injection element may be fixed so that it permanently protrudes through the housing. In these circumstances the injection element may be protected by a removable guard to minimise any danger of the element being damaged, or accidentally damaging something else, before use of the device. It will also be appreciated that in these circumstances the injection element is generally introduced into the patient's body tissue as the device is placed against the patient's skin, rather than as a subsequent step as described above. The injection element may comprise the cannula 6 described above or may comprise a needle. As indicated above, in one example the injection element comprises a trocar (which does not have a bore) of a cannula arrangement which leaves a flexible tube in the tissue of the user but does not leave the needle in the user during the medicament delivery.

The heat exchanger 24 has been described principally in terms of operating under the control of an electronic controller 16. However, the heat exchanger 24 may alternatively operate without the electronic controller 16. For example, operations of the heat exchanger 24 may be triggered or otherwise controlled by a timing element such as a mechanical timer in the device 1. The timing element may be relatively simple and may comprise a count-down timer. The elapse of a fixed count-down period of the timing element may cause the heat exchanger 24 to operate in a particular manner, for example by opening or closing the valves 30 at the entry and exit ports 26, 27 to admit or release medicament.

The timing element may be configured to count down the fixed count-down period in response to the initial activation of the device 1 by the patient (e.g. following operation of the switch 38 referred to above). Alternatively, the timing element may be configured to count down the fixed count-down period in response to the extension of the cannula 6 or other injection element from the housing 2. Alternatively, the timing element may be configured to count down the fixed count-down period in response to the attachment of the contact region 21 of the device 1 to the body of the patient.

One or more suitable proximity sensors in the contact region 21 may be used to determine when the device 1 has been attached. The connection between the timing element and the heat exchanger 24 may be mechanical or electrical.

This type of timer-based configuration of the heat exchanger 24 may be particularly applicable if the device 1 does not comprise the central controller 16 described above. The same is true for operation of other components of the device 1, such as the flow control apparatus 17, which may similarly be triggered into operation by a relatively simple timing element.

In addition to the heat exchanger 24, the device 1 may comprise a material or structure configured to enhance the transfer of thermal energy to the medicament. This material or structure may be configured to release thermal energy in response to a trigger, which may be initiated by the patient. Some or substantially all of the released thermal energy may be transferred into the medicament, for example through the heat exchanger 24. The material or structure may be located adjacent to the patient interface surface 25 referred to above.

An example of such a material or structure is one which releases thermal energy in an exothermic reaction. The material or structure may, for example, comprise iron and the release of thermal energy may be as a result of the exothermic oxidation of the iron when exposed to air. The patient may trigger the oxidation exposing the material or structure to air. This may be achieved, for example, by removing a seal, such as the protective covering on the contact region 21, from the material or structure.

Alternatively, the material or structure may release thermal energy as a result of an exothermic crystallisation of a supersaturated solution, such as sodium acetate. The patient may trigger the crystallisation by flexing or applying pressure to the material in order to create nucleation centres.

The device 1 is described above as being configured to deliver the medicament subcutaneously. However, it may instead be configured for intradermal injection, for instance using a microneedle, or for injection in some other manner.

The bolus injector device may be of the type known as a Large Volume Device (LVD). An LVD injection device is configured to dispense a relatively large dose of medicament, in particular at least 1 ml and typically up to 2.5 ml, but possibly up to 10 ml.

The bolus injector device is configured to deliver a bolus of the respective medicament to bring a volume of the medicament into a patient's body within a predetermined time. The injection rate, however, may not be critical, i.e. tight control may not be necessary. However, there may be an upper (physiological) limit to the delivery rate in order to avoid damage to the tissue surrounding the delivery site. The time taken to deliver a bolus dose of medicament may be between a few minutes and many hours depending on a number of factors including the quantity (volume) of medicament, the viscosity of the medicament and the nature of the injection site at which the injection device is intended to be used.

From a user or Health Care Professional perspective, it is desirable for an injection device to be configured to minimally impact the patient's lifestyle and schedule, providing the patient with minimal reminder of his or her disease between the injections. The treatment schedule for therapies is usually intermittent, i.e. may be one injection per week, one injection every other week, or one per month. Therefore, the patient usually has no routine in dealing with his or her disease, and hence has minimal routine/experience in performing the required injections. Thus, configuration of the injection device to simplify its operation by patients is highly desirable.

Because it is intended for bolus operation, the configuration of the injection device is quite different compared to an injection device that is intended to be used for basal operation. Also, its use is quite different. For instance, a basal type insulin pump generally is relatively expensive as it includes many sophisticated diabetes specific features like programmable delivery rate profiles, bolus calculators etc. Further, the connection to the body via an infusion set allows the patient to handle and manipulate the pump in his/her field of view while the therapy is ongoing. Further, diabetes patients usually have a routine in setting-up the infusion set, connecting and operating the pump, and disconnecting the pump temporarily for events like taking a shower so not to expose the pump to water. In contrast, the bolus injector devices described above can be relatively simple and inexpensive devices. They may be provided as single-use devices, which cannot be recharged with medicament, which further reduces complexity and cost.

The actuators referred to above may comprise mechanical actuators, for example comprising one or more sprung elements. The actuators may alternatively comprise solenoids, piezo actuators, magnetic actuators or other mechanisms.

The flow of medicament through the device may controlled by one or more valves (not shown), particularly if the reservoir of medicament is pressurized in the capsule 5.

The term "drug" or "medicament", as used herein, means a pharmaceutical formulation containing at least one pharmaceutically active compound. In some embodiments, the pharmaceutically active compound can have a molecular weight up to 1500 Da or may include a peptide, a protein, a polysaccharide, a vaccine, a DNA molecule, an RNA molecule, an enzyme, an antibody or a fragment thereof, a hormone or an oligonucleotide, or a mixture of the above-mentioned pharmaceutically active compound. Various types or subtypes of compounds are also contemplated. For example, RNA may include RNAi, siRNA, or miRNA. In other embodiments, the pharmaceutically active compound can be useful for the treatment or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis or rheumatoid arthritis. In some embodiments, the pharmaceutically active compound can comprise at least one peptide for the treatment or prophylaxis of diabetes mellitus or complications associated with diabetes mellitus such as diabetic retinopathy. The pharmaceutically active compound can also comprise at least one human insulin or a human insulin analogue or derivative, glucagon-like peptide (GLP-1) or an analogue or derivative thereof, or exendin-3 or exendin-4 or an analogue or derivative of exendin-3 or exendin-4 or a pharmaceutically acceptable salt or solvate thereof.

Insulin analogues can include, for example, Gly(A21), Arg(B31), Arg(B32) human insulin; Lys(B3), Glu(B29) human insulin; Lys(B28), Pro(B29) human insulin; Asp (B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives can include, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 can include, for example, Exendin-4(1-39).

Hormones can include, for example, hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, or Goserelin.

A polysaccharide can include, for example, a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies can include generally globular plasma proteins (~150 kDa) that are also known as immunoglobulins which share a basic structure. As they can have sugar chains added to amino acid residues, they may also be classified as glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that can include four polypeptide chains; two heavy chains and two light chains connected by disulfide bonds between cysteine residues. Each heavy chain can be about 440 amino acids long; each light chain can be about 220 amino acids long. Heavy and light chains may each contain intra-chain disulfide bonds which stabilize their folding. Each chain is composed of structural domains called Ig domains. These domains typically contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of antibodies can be similar, the unique property of a given antibody is determined by the variable (V) regions, as detailed above. More specifically, variable loops, often three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is usually the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their inter-chain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H inter-chain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion. Pharmaceutically acceptable solvates are for example hydrates.

In some embodiments, medicaments of various viscosities can be injected. For example, viscosity could range from about 3 to about 50 cP. In other embodiments, viscosity could be less than about 3 cP or greater than about 50 cP. Injection can further include delivering a medicament to a sub-cutaneous, an intra-muscular, or a transdermal location within a patient's body. The medicament can be in the form of a liquid, gel, slurry, suspension, particle, powder, or other type.

Typical injection volumes can range from about 1 mL to about 10 mL. Rates of injection may be about 0.5 mL/min, about 0.2 mL/min, or about 0.1 mL/min. Such injection profiles may be generally constant in flow rate, generally continuous in duration, or both generally constant and generally continuous. These injections can also occur in a single step of administration. Such injection profiles may be referred to as bolus injections.

Delivery devices functioning with such medicaments may utilize a needle, cannula, or other injection element configured to deliver a medicament to the patient, as previously discussed. Such an injection element may, for example, have an external size or diameter of 27 G or less. Further, the injection element could be rigid, flexible, and formed using a range of one or more materials. And in some embodiments, the injection element may include two or more components. For example, a rigid trocar may operate in conjunction with a flexible cannula as previously discussed. Initially, both the trocar and cannula may move together to pierce the skin. The trocar may then retract while the cannula remains at least partially within the target tissue. Later, the cannula may separately retract into the delivery device.

The insertion mechanism for inserting the insertion element may take any suitable form. As described above, it may be a mechanical spring based mechanism. Alternatively, the insertion element mechanism may for instance include an electric motor and a gear mechanism that causes insertion of the insertion element into the user. Alternatively, the insertion mechanism may be a gas or fluid pressure operated mechanism, in which case the needle driving energy source is either a reservoir of pressurised gas or a chemical system in which two or more chemicals are mixed together to produce gas or fluid pressure.

The invention claimed is:

1. A device configured to deliver a medicament to a user by injection, comprising:
    a reservoir configured to hold the medicament;
    an injection element configured to inject the medicament from the device into a patient; and
    a heat exchanger configured to extract thermal energy from a body tissue of the user through a contact surface of the heat exchanger when the contact surface is in contact with a portion of skin of the user and to supply the extracted thermal energy to increase a temperature of the medicament,
        wherein the heat exchanger comprises a medicament flow path formed of thermally conductive material forming, at least part of, the contact surface that in use is supported against a portion of skin of the user, and
        wherein the medicament flow path comprises a winding path.

2. The device according to claim 1, wherein the medicament flow path comprises a liquid impermeable membrane to allow gas but not liquid medicament to be expelled through the membrane.

3. The device according to claim 1, wherein the heat exchanger comprises a Peltier element.

4. The device according to claim 3, wherein the medicament is thermally coupled to the Peltier element to act as a heat sink for the thermal energy extracted from the body tissue of the user by the Peltier element.

5. The device according claim 1, further comprising a medicament temperature sensor configured to sense a temperature of the medicament in the device.

6. The device according to claim 5, wherein the device is configured to commence delivery of the medicament in response to the temperature sensor sensing that the medicament has reached a predetermined temperature.

7. The device according to claim 5, wherein the device comprises a flow control apparatus configured to control a rate of delivery of the medicament in response to the temperature of the medicament sensed by the temperature sensor.

8. The device according to claim 7, wherein the flow control apparatus is configured to increase the rate of delivery in a manner which is proportional to increases in the temperature of the medicament sensed by the temperature sensor.

9. The device according to claim 7, wherein the flow control apparatus is configured to decrease the rate of delivery in a manner which is proportional to decreases in the temperature of the medicament sensed by the temperature sensor.

10. The device according to claim 7, wherein the flow control apparatus comprises a flow restrictor element located in the heat exchanger, the flow restrictor element configured to vary the size of a flow path through the device to vary the rate of delivery of the medicament.

11. The device according to claim 7, wherein the flow control apparatus comprises a medicament pump configured to pump medicament through the heat exchanger.

12. The device according to claim 1, wherein the medicament comprises a pharmaceutically active compound.

13. The device of claim 1, wherein the medicament flow path forms a loop.

14. A system comprising:
    a device configured to deliver a medicament to a user by injection, comprising:
        an injection element configured to inject the medicament from the device into a patient;
        a heat exchanger configured to extract thermal energy from a body tissue of the user through a contact surface of the heat exchanger when the contact surface is in contact with a portion of skin of the user and to supply the extracted thermal energy to increase a temperature of the medicament; and
        a reservoir of medicament to be delivered into the user by injection,
    wherein the heat exchanger comprises a medicament flow path formed of thermally conductive material forming, at least part of, the contact surface that in use is supported against a portion of skin of the user, and
    wherein the medicament flow path comprises a winding path.

15. The system of claim 14, wherein the device further comprises a medicament temperature sensor configured to sense a temperatures of the medicament in the device.

16. A method of increasing a temperature of a medicament in a device configured to deliver the medicament to a user by injection, comprising:
    extracting thermal energy from a body tissue of the user using through a contact surface of a heat exchanger when the contact surface is in contact with a portion of skin of the user, the heat exchanger comprising a medicament flow path formed of thermally conductive material forming, at least part of, the contact surface, wherein the medicament flow path comprises a winding path; and
    supplying the extracted thermal energy to increase the temperature of the medicament.

17. The method of claim 16, further comprising sensing a temperature of the medicament in the device using a temperature sensor.

18. The method of claim 17, further comprising controlling a rate of delivery of the medicament in response to the temperature of the medicament sensed by the temperature sensor.

* * * * *

UNITED STATES PATENT AND TRADEMARK OFFICE
CERTIFICATE OF CORRECTION

PATENT NO. : 10,369,298 B2  
APPLICATION NO. : 15/509407  
DATED : August 6, 2019  
INVENTOR(S) : Christian Nessel Page 1 of 1

It is certified that error appears in the above-identified patent and that said Letters Patent is hereby corrected as shown below:

In the Claims  
Column 17, Line 55, Claim 5, after "according", insert -- to --.

Signed and Sealed this  
Seventeenth Day of December, 2019

Andrei Iancu  
*Director of the United States Patent and Trademark Office*